(12) United States Patent
Patel et al.

(10) Patent No.: US 9,176,021 B2
(45) Date of Patent: Nov. 3, 2015

(54) LEAK DETECTION DEVICE USING HYDROGEN AS TRACER GAS

(75) Inventors: Ketan Patel, Annecy le Vieux (FR); Frederic Rouveyre, Chavanod (FR)

(73) Assignee: ADIXEN VACUUM PRODUCTS, Annecy (FR)

( * ) Notice: Subject to any disclaimer, the term of this patent is extended or adjusted under 35 U.S.C. 154(b) by 230 days.

(21) Appl. No.: 13/328,377

(22) Filed: Dec. 16, 2011

(65) Prior Publication Data

US 2012/0318048 A1    Dec. 20, 2012

(30) Foreign Application Priority Data

Dec. 17, 2010  (FR) ........................ 10 60729

(51) Int. Cl.
*G01M 3/02*  (2006.01)
*G01M 3/20*  (2006.01)
*G01N 33/00*  (2006.01)

(52) U.S. Cl.
CPC ............... *G01M 3/20* (2013.01); *G01N 33/005* (2013.01)

(58) Field of Classification Search
CPC ....... G01M 3/20; G01M 3/226; G01M 3/229; G01M 3/22; G01N 33/005; G01N 27/129
USPC ......................... 73/40.7, 49.3, 49.2
See application file for complete search history.

(56) References Cited

U.S. PATENT DOCUMENTS

| | | |
|---|---|---|
| 3,939,695 A | 2/1976 | Booth |
| 5,150,605 A * | 9/1992 | Simpson ................ 73/49.3 |
| 5,293,771 A | 3/1994 | Ridenour |
| 5,386,717 A * | 2/1995 | Toda ..................... 73/40.7 |
| 5,932,797 A * | 8/1999 | Myneni .................. 73/40.7 |
| 6,160,278 A * | 12/2000 | Liu et al. ................ 257/252 |
| 6,279,384 B1 * | 8/2001 | Heikkinen et al. ........ 73/40.7 |
| 6,314,793 B1 | 11/2001 | Webb et al. |
| 7,389,675 B1 * | 6/2008 | Hunter et al. ............ 73/31.06 |

(Continued)

FOREIGN PATENT DOCUMENTS

| | | |
|---|---|---|
| CN | 2051351 U | 1/1990 |
| DE | 19853049 A1 | 6/2000 |

(Continued)

OTHER PUBLICATIONS

French Preliminary Search Report for FR 1060729 dated Aug. 11, 2011.

(Continued)

*Primary Examiner* — Peter Macchiarolo
*Assistant Examiner* — Natalie Huls
(74) *Attorney, Agent, or Firm* — Sughrue Mion, PLLC (57) ABSTRACT

The leak detection device using hydrogen as a tracer gas is intended to be connected to an object to be tested. The leak detection device includes a hydrogen sensor placed in a low-pressure enclosure and includes a diode, a resistor, a MOS-type transistor whose gate is covered with a palladium catalyst, a pump connected to the low-pressure enclosure, a pressure gauge configured to measure the pressure in a vacuum line formed by the low-pressure enclosure connected to the pump, and a multiway valve having a first port allowing admission of the gas flow containing the tracer gas into the vacuum line, and a second port allowing the admission of neutral gas. The method makes it possible to stabilize the pressure of the vacuum line in order to avoid fluctuations in the hydrogen measurements.

16 Claims, 5 Drawing Sheets

(56) References Cited

U.S. PATENT DOCUMENTS

| | | | |
|---|---|---|---|
| 7,448,256 B2* | 11/2008 | Jenneus et al. | 73/49.2 |
| 7,717,681 B2* | 5/2010 | Bohm et al. | 417/248 |
| 7,980,117 B2* | 7/2011 | Wetzig et al. | 73/40.7 |
| 2007/0157704 A1 | 7/2007 | Jenneus et al. | |
| 2009/0277249 A1* | 11/2009 | Polster et al. | 73/40.7 |
| 2010/0313634 A1* | 12/2010 | Wetzig | 73/40.7 |
| 2011/0197659 A1* | 8/2011 | Palten et al. | 73/40.7 |
| 2012/0153360 A1* | 6/2012 | Patel et al. | 257/253 |

FOREIGN PATENT DOCUMENTS

| | | |
|---|---|---|
| JP | 2005-164525 A | 6/2005 |
| JP | 2006-317196 A | 11/2006 |
| JP | 2007-519929 A | 7/2007 |
| WO | WO 97/39322 A1 | 10/1997 |
| WO | WO 2005/054806 A1 | 6/2005 |
| WO | 2005/073707 A1 | 8/2005 |

OTHER PUBLICATIONS

Communication dated Jul. 21, 2015, issued by the Japanese Intellectual Property Office in counterpart Japanese Application No. 2011-274097 with English translation.

* cited by examiner

LEAK DETECTION DEVICE USING HYDROGEN AS TRACER GAS

The present invention relates to a device for detecting large leaks, for example ranging from a few $Pa.m^3/s$ to $10^{-6}$ $Pa.m^3/s$, by the spraying technique.

The technique of leak detection by spraying consists in placing the object to be tested in a leaktight enclosure whose atmosphere mainly contains a tracer gas. The gas inside the object is evacuated to a low pressure, for example of the order of 10 hPa. The presence of large leaks is then tested by detecting the pointwise presence of the tracer gas inside the object, which is placed in the test enclosure, with the aid of a leak detector. The internal atmosphere of the object to be tested is connected to a tracer gas detector. A plurality of leak detection methods are known.

A first method uses helium as the tracer gas and a mass spectrometer as the detector. This makes use of the property of helium that it passes through small leaks more easily than other gases owing to the small size of its molecule. This method therefore has high sensitivity, and it is conventionally used to detect leaks ranging from $10^{-5}$ to $10^{-12}$ $Pa.m^3/s$. However, the helium method has the drawbacks of the high cost of the tracer gas and the need to create a vacuum inside the object to be tested, in order to allow the mass spectrometer to operate. In order to maintain a very low pressure, a large and expensive pumping unit is necessary. Furthermore, when the object to be tested has a large volume, it may be difficult or even impossible to reach the required pressure level. Even if the required pressure level can be reached, the pumping cycle is very long. When the leakage rate is very high, there is a risk that damage will be incurred in the mass spectrometer. The filament of the mass spectrometer may become polluted and even break. Lastly, the maintenance of such a complicated system is very expensive.

In order to overcome these drawbacks, a method using hydrogen as the tracer gas has been developed. Hydrogen has the advantage of a much more rapid diffusion rate inside the objects under test, and it dissipates more rapidly than helium. It is much less expensive than helium, and the detection is carried out by different types of sensors operating at atmospheric pressure. For this reason, this method constitutes a highly advantageous alternative for industry because it is less expensive and simpler to implement. However, this method has a lower sensitivity than the helium method, which limits its use.

It is an object of the present invention to provide a leak detection device which makes it possible to detect large leaks of up to $10^{-6}$ $Pa.m^3/s$ with good sensitivity.

The invention also provides a leak detection device which is robust, lightweight and inexpensive.

The present invention relates to a device for leak detection by means of hydrogen as a tracer gas, which is intended to be connected to an object to be tested and comprises a hydrogen sensor placed in a low-pressure enclosure and comprising a diode, a resistor, and a MOS-type transistor whose gate is covered with a palladium catalyst, a pumping means connected to the low-pressure enclosure, a pressure gauge configured to measure the pressure in a vacuum line formed by the low-pressure enclosure connected to the pumping means, and a multiway valve comprising a first port allowing admission of the gas flow containing the tracer gas into the vacuum line, and a second port allowing the admission of gas, this second port being configured to control the pressure in the vacuum line as a function of the pressure gauge.

The term multiway valve refers to any means comprising one or more valves configured to control the communication between at least three ports: a first port communicating with the object to be tested, a second port communicating with the sensor and at least a third port for the admission of e.g. air.

According to a first embodiment, the second port is configured to be open to the external atmosphere.

According to a second embodiment, the device furthermore comprises a particle filter interposed between the sensor and the multiway valve in order to filter the dust particles contained in the gas before it enters into contact with the hydrogen sensor.

According to a third embodiment, the device furthermore comprises an electronic control module configured to receive the value of the pressure of the vacuum line measured by the pressure gauge, and to receive a setpoint value, and configured to control the admission of neutral gas as a function of these values.

According to a fourth embodiment, the device furthermore comprises a mathematical model for calculating the leakage rate on the basis of the variation of the drain-source voltage of the transistor contained in the sensor as a function of time.

According to a fifth embodiment, the device furthermore comprises a circuit for balancing the voltage of the resistor of the sensor.

The circuit for balancing the voltage of the resistor of the sensor is advantageously configured to maintain a fixed temperature independently of the value of the pressure in the low-pressure enclosure.

The fixed temperature is comprised, for example, between 100° C. and 250° C.

The pressure in the low-pressure enclosure is comprised, for example, between 100 Pa and 5000 Pa.

The invention also relates to a method for leak detection of an object to be tested by means of a leak detection device as described above, wherein the pressure of the vacuum line is controlled by controlling the admission of the neutral gas into the vacuum line through the second admission port of the multiway valve.

According to one embodiment, the admission of the neutral gas is controlled by controlling the second port automatically as a function of the measurement of the pressure and the value of the predetermined setpoint.

The present invention has numerous advantages. The detection device has a very high sensitivity at very low pressure for leakage rates of up to $10^{-6}$ $Pa.m^3/s$. The hydrogen sensor can be used at a low pressure of between 100 Pa et 5000 Pa, for example 1000 Pa (10 mbar), which is a pressure easily reached with a small diaphragm vacuum pump, for example, and does not require an expensive and bulky high-power pumping unit. The hydrogen sensor is economical to manufacture and has a long lifetime. It can be replaced easily if necessary. This hydrogen sensor allows the detection device to be lightweight and compact, and therefore easy to transport. It is easy to integrate into existing apparatus comprising a leak detection device.

The invention may be applied to all types of object, but more especially to the chambers used for fabrication in industry which do not require a very strong vacuum, for example vacuum ovens for the treatment of materials or coating deposition (for example for the lenses of sunglasses).

Other characteristics and advantages of the present invention will become apparent on reading the following description of an embodiment, which is of course given by way of illustration and without implying limitation, and in the appended drawing in which

In FIGS. 6, 7 and 9, the pressure variation $\Delta V$ over time is plotted in mV/s on the ordinate as a function of the leakage rate L in $mbar.l.s^{-1}$ on the abscissa.

In these figures, elements which are identical have the same reference numbers.

Figure 1:
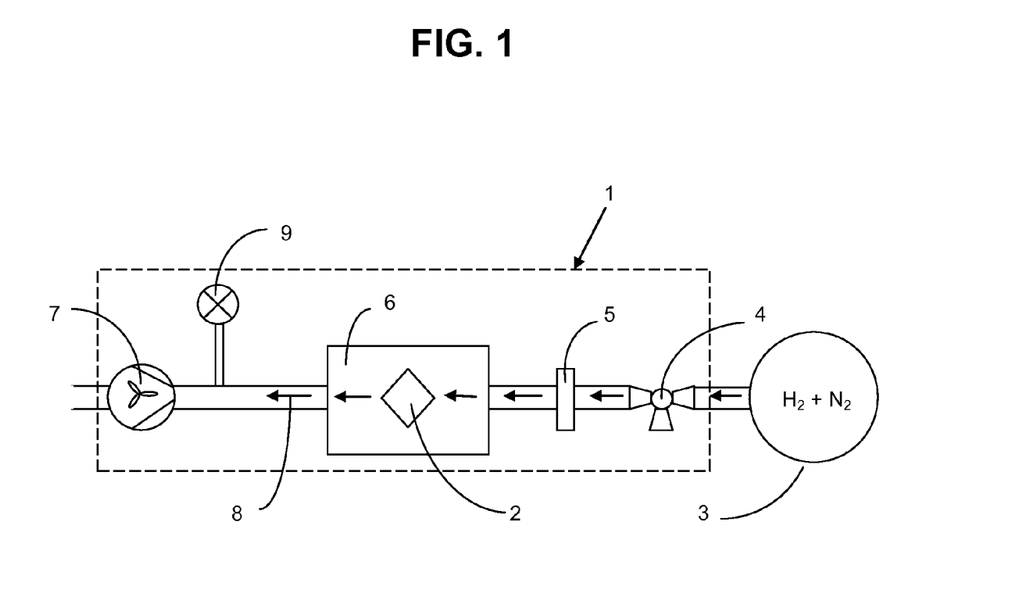
FIG. 1 illustrates a first embodiment of a leak detection device in detection configuration.

In the embodiment illustrated in FIG. 1, the leak detection device 1 comprises a hydrogen sensor 2 connected to the internal atmosphere of an object 3 to be tested. The detection device 1 comprises a multiway valve, which may in particular be a three-way valve 4, controlling the communication of the hydrogen sensor 2 with the object 3 to be tested in order to allow admission of the gas flow containing the tracer gas into the leak detection device 1, and a particle filter 5 interposed between the sensor 2 and the three-way valve 4 in order to filter the dust particles contained in the gas before it comes into contact with the hydrogen sensor 2. The presence of the filter 5 makes it possible to protect the sensor 2 and extend its lifetime. According to a variant, the three-way valve 4 may be used to regulate the entry of air in order to maintain a low pressure of between 100 Pa and 5000 Pa, for example 1000 Pa, in the vacuum line formed by a low-pressure enclosure 6 connected to a pumping means 7. As an alternative, the three-way valve 4 may be arranged after the sensor.

The hydrogen sensor 2 is placed in the low-pressure enclosure 6 connected to the pumping means 7, which makes it possible on the one hand to reach and maintain a low pressure in the low-pressure enclosure 6, for example 1000 Pa, and on the other hand to create a gas flow 8 in the detection device 1. The pumping means 7 making it possible to lower the pressure is placed downstream of the hydrogen sensor 2, on the opposite side from the arrival of the gas coming from the object 3 to be tested, in order to create circulation of the gas 8. There is thus no accumulation of gas upstream of the sensor 2, and only the hydrogen molecules coming from the leak to be measured come into contact with the hydrogen sensor 2. This configuration has the advantage of increasing the response time of the sensor 2. The hydrogen sensor 2 is preferably arranged so that the head of the sensor 2 faces the gas flow 8 containing hydrogen coming from the object 3 to be tested and pumped by the pumping means 7, so as to increase the sensitivity of the hydrogen sensor 2. The pumping means 7 may be of any type, such as a vacuum pump, for example a diaphragm vacuum pump; in particular, a diaphragm vacuum pump with the reference "AMD4" marketed under the brand "ADIXEN" will preferably be selected. A pressure gauge 9, such as a manometer, mounted on the duct connecting the low-pressure enclosure 6 and the pumping means 7, makes it possible to monitor the pressure reached in the low-pressure enclosure 6.

In order to measure the leak, the inlet of the detection device 1 is connected to the object 3 to be tested. The pumping means 7 lowers the pressure in the vacuum line.

The three-way valve 4 is then progressively opened. The leak detection device comprises an electronic control module configured to receive the value of the pressure of the vacuum line measured by the pressure gauge 9, configured to receive a setpoint value and configured to control the admission of neutral gas as a function of these values. The electronic control module makes it possible to ensure that a stable pressure, for example 1000 Pa, is reached in the vacuum line, this being in order to avoid fluctuations in the measurement of the leak. The measurement can then begin. The exterior of the object 3 to be tested is sprayed with a gas, composed for example of a mixture of 95% nitrogen and 5% hydrogen. Under the effect of the pumping, part of this gas passes through the wall of the object 3 to be tested, at the position of the leak, and enters the leak detection device 1. The gas spraying is carried out step by step on each region of the external surface of the object 3 to be tested, with a waiting time of a few seconds between each step in order to allow time for the pumped gas to reach the hydrogen sensor 2.

An electronic means for regulating the temperature may be added to the leak detection device so that the temperature does not influence the pressure.

Figure 2:
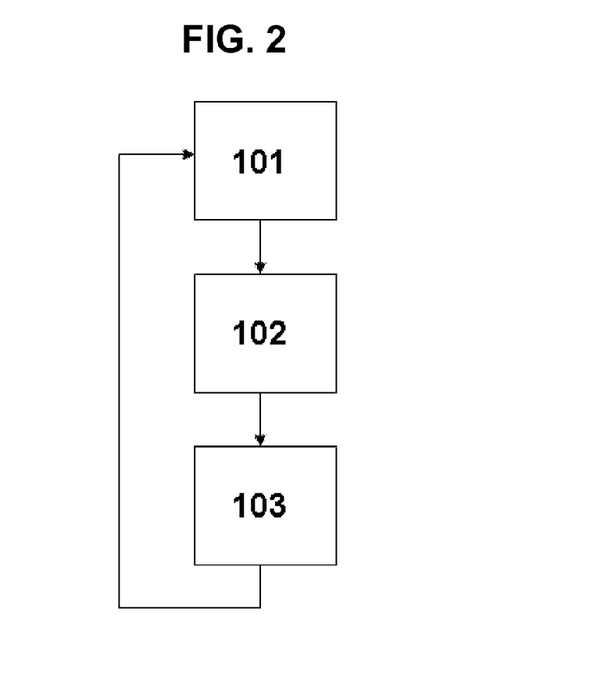
FIG. 2 illustrates the method for stabilizing the pressure of the vacuum line.

Steps of the method for maintaining a stable pressure are represented in FIG. 2. In a first step 101, the pressure of the vacuum line is measured by using the pressure gauge 9. In a second step 102, the electronic control module compares the pressure value measured by the gauge 9 with a setpoint pressure value. In a third step 103, the electronic control module causes the second gas admission port to open or close so that the pressure of the vacuum line reaches the setpoint pressure value. This method is repeated in a loop during the leak measurement. The admission of gas takes place automatically as a function of the measured pressure and the predetermined setpoint pressure value.

Figure 3:
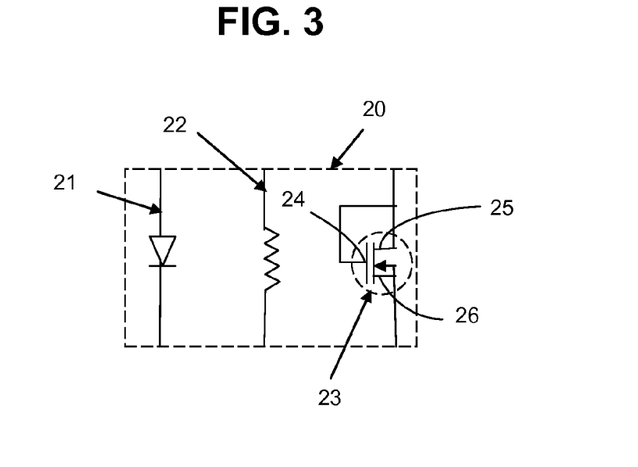
FIG. 3 illustrates an embodiment of a hydrogen sensor.

FIG. 3 will now be considered, which represents an embodiment of a hydrogen sensor 20. The sensor 20 comprises a diode 21, a resistor 22 and a transistor 23, which are interconnected. The transistor 23 is a field effect transistor of the MOSFET type ("Metal Oxide Semiconductor Field Effect Transistor"). The transistor 23 is of the "n" type and has three active electrodes: the gate 24, the drain 25 and the source 26. The gate 24 is connected to the drain 25. The transistor 23 modulates the current which flows through it by means of a signal applied to the gate 24, making it possible to control the voltage between the drain 25 and the source 26. The gate 24 is covered with a catalyst based on palladium. When the $H_2$ molecule arrives in contact with the palladium catalyst of the gate 24, it is cleaved to give $H^+$ ions. The $H^+$ ions diffuse through the catalyst and become trapped on the gate 24 of the transistor 23. This causes a variation in the drain 25-source 26 resistance of the transistor 23. The drain 25-source 26 resistance of the transistor 23 thus constitutes the core of the sensor fulfilling the function of measuring the leak. By injecting a constant current into the drain 25 of the transistor 23, a voltage V is obtained representing the quantity of $H^+$ ions trapped by the gate 24, which makes it possible to evaluate the flow of hydrogen arriving in contact with the gate 24.

An electronic control module comprises in particular electronic circuits for driving the leak detection device, and a mathematical model for calculating the leakage rate. The mathematical model has been developed to give a measurement of the leakage rate on the basis of the variation in the drain 25-source 26 voltage of the transistor 23 as a function of time, which is linked with the hydrogen sensitivity of the sensor 20. It is possible to add an automatic calibration option, with a fixed leakage rate, based on this mathematical model. Since the number of hydrogen atoms which strike the active surface of the gate 24 of the transistor 23 is proportional to the pressure in the low-pressure enclosure 6, the drain 25-source 26 resistance will be proportional to the absolute hydrogen pressure around the transistor 23 in the low-pressure enclosure 6. With a residual pressure of 1000 Pa, a monolayer of hydrogen atoms is formed in about 25 μs.

A heating resistor 22 makes it possible to heat the hydrogen sensor 20 to a temperature of 130° C., for example. A temperature of this order advantageously increases the sensitivity of the hydrogen sensor 20. The temperature must not however exceed 250° C., this limit being imposed by the silicon of the transistor 23. Tests have shown that a temperature of 180° C. can be used without damage. By way of example, the heating resistor of the hydrogen sensor 20 may have a value of between 70 Ω and 80 Ω; at atmospheric pressure, the heating current will be from 60 to 80 mA, i.e. a heating power of approximately 0.4 W.

A diode 21 is used for measuring the temperature of the hydrogen sensor 20; it is possible for this diode to be supplied with a current of 1 mA when the voltage across its terminals reaches 590 mV. This value of the voltage corresponds to a temperature of 130° C. The temperature coefficient of the diode is −1.6 mV/K.

For reasons of safety, a gas mixture composed of 95% nitrogen and 5% hydrogen is used, which is not brought into contact with the hydrogen sensor 20 until the temperature of 130° C. has been reached, in order to avoid any degradation of the catalyst. It is also in order to preserve the catalyst that the hydrogen sensor 20 is used at very low pressure, so as to be in contact with only a small quantity of hydrogen.

After the measurement, the hydrogen sensor 20 may be cleaned by injecting a gas mixture containing 5% hydrogen for about 10 seconds, with a temperature rise promoting recovery of the catalyst after saturation.

Figure 4:
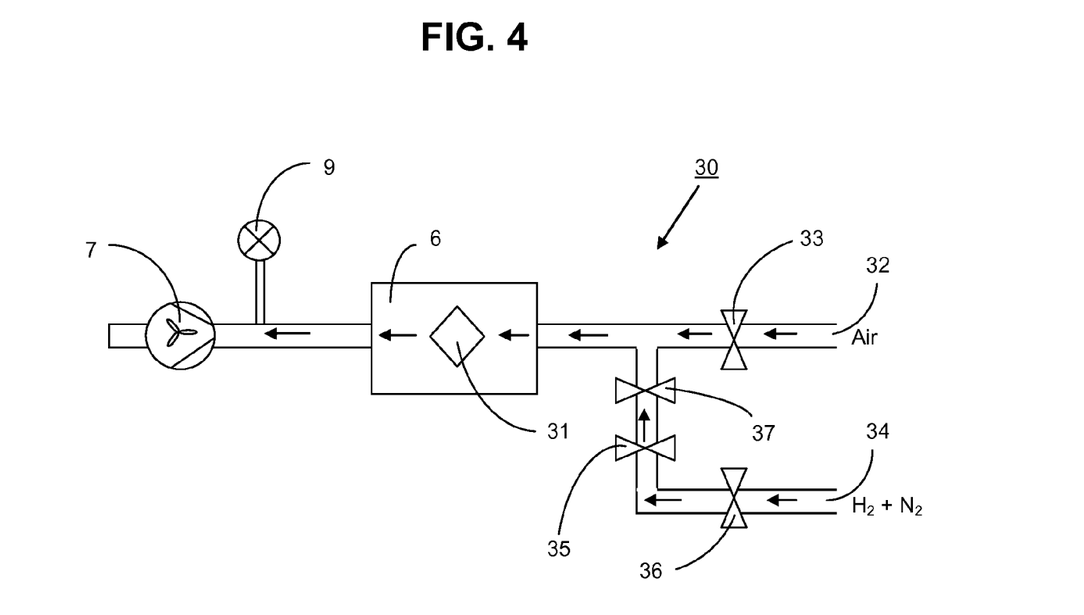
FIG. 4 illustrates an example of a test device intended to evaluate the sensitivity of a hydrogen sensor.

FIG. 4 illustrates a test device 30 intended to evaluate the sensitivity of a hydrogen sensor 31 to the pressure in the test device 30. The test device 30 comprises a hydrogen sensor 31 placed in a low-pressure enclosure 6 connected to a pumping means 7 by a duct, the low-pressure enclosure and the duct together forming a vacuum line. The pressure in the vacuum line is controlled on the basis of the measurement carried out by a pressure gauge 9. The test device 30 comprises an air inlet 32 controlled by an admission valve 33. The test device 30 also comprises an inlet 34 for tracer gas, here a gas mixture composed of 95% nitrogen and 5% hydrogen, the flow of which is regulated by a microvalve 35. A first shut-off valve 36 and a second shut-off valve 37, arranged on either side of the microvalve 35, are operated manually in order to permit or interrupt the flow of tracer gas. The air inlet 32 and the inlet for tracer gas 34 communicate through a common duct with the low-pressure enclosure 6 containing the hydrogen sensor 31.

First, the sensitivity of the hydrogen sensor 31 to the pressure in the vacuum line was evaluated. The vacuum line is maintained at low pressure, for example 1000 Pa, by virtue of the pumping means 7 on the one hand and on the other hand the pressure gauge 9, which controls the admission valve 33 allowing introduction of air if necessary in order to re-establish the pressure at the fixed value. The resistor of the sensor 31 is used to heat the hydrogen sensor 31 to 130° C. in order to improve its sensitivity.

Figure 5:
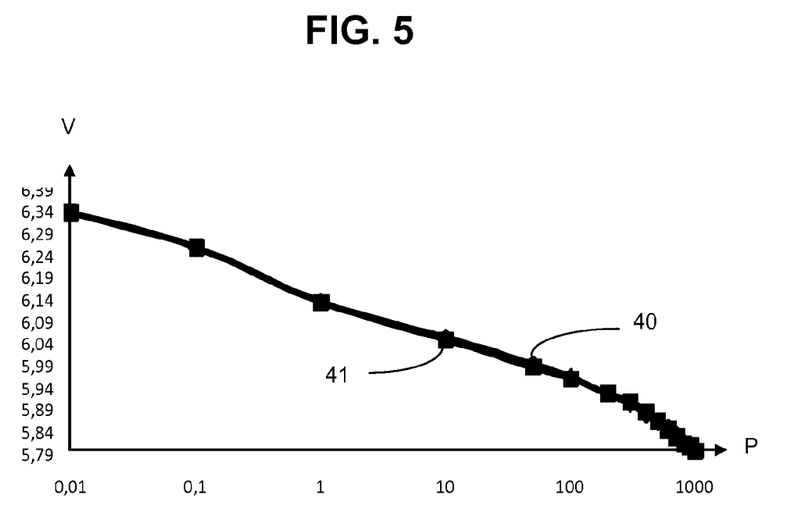
FIG. 5 illustrates the result of a sensitivity test of a hydrogen sensor as a function of the pressure in the test device: the voltage V of the resistor of the hydrogen sensor in volts is plotted on the ordinate and the pressure P in mbar is plotted on the abscissa.

FIG. 5 illustrates the sensitivity of the voltage of the resistor of the sensor 31 as a function of the pressure in the low-pressure enclosure 6. A good reproducibility of the measurement and a high sensitivity of the hydrogen sensor 31 to the pressure are observed, with the rising 40 and falling 41 curves coinciding. This test confirms that the voltage of the resistor of the sensor 31 is sensitive to the pressure. If the pressure varies, a variation in the resistor voltage will be produced, which will lead to a temperature change of the hydrogen sensor. This will be manifested by a modification of the sensitivity of the hydrogen sensor 31, and therefore a change in the leak value detected. Because of this sensitivity, the circuit for balancing the voltage has been produced so that the sensor 31 is always heated to the same temperature, regardless of the pressure.

Figure 6:
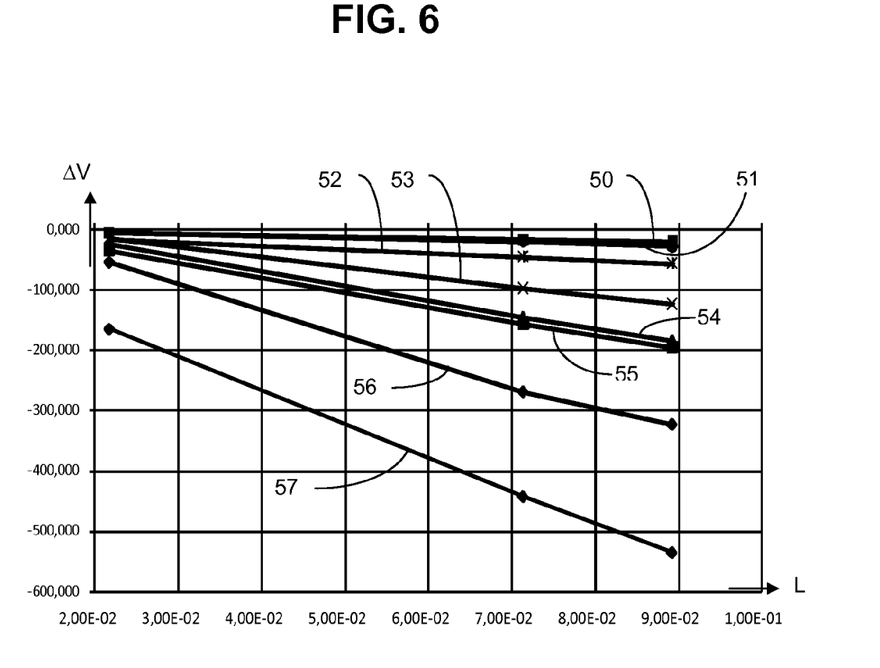
FIG. 6 illustrates the result of a sensitivity test of the hydrogen sensor for different values of the leakage rate and the pressure in the test device.

Secondly, the sensitivity of the hydrogen sensor 31 to different pressures P in the vacuum line and for different leakage rates was evaluated. FIG. 6 shows the voltage variation ΔV over time, in mV/s, and as a function of a plurality of values of the leakage rate L. The test was carried out with the following pressures P in the vacuum line:

| | |
|---|---|
| P = 850 mbar | curve 50 |
| P = 500 mbar | curve 51 |
| P = 200 mbar | curve 52 |
| P = 100 mbar | curve 53 |
| P = 50 mbar | curve 54 |
| P = 20 mbar | curve 55 |
| P = 10 mbar | curve 56 |
| P = 5 mbar | curve 57 |

The tracer gas containing hydrogen, which is representative of a leak, is injected into the test device 30 at a rate imposed by the microvalve 35, which has been calibrated beforehand. When the microvalve 35 and the shut-off valves 36, 37 are opened, the flow of tracer gas comes into contact with the hydrogen sensor 31 and the voltage of the transistor of the hydrogen sensor 31 decreases. When the microvalve 35 and the shut-off valves 36, 37 are closed, the flow of tracer gas is interrupted and the voltage of the transistor of the hydrogen sensor 31 increases. The variations in the slope of the increase and decrease curves of the voltage are measured and analyzed in order to determine a leakage rate.

The test was carried out in the following way. The supply of the sensor is started. The sensor is supplied with a diode voltage of 0.574 V and a transistor current of 0.1 mA, which corresponds to a temperature of 130° C. Throughout the duration of the test, the output voltage of the diode, which is representative of the stability of the temperature, and the output voltage of the transistor are measured and recorded. The output voltage of the diode remained stable during the test, which demonstrates excellent control of the temperature of the hydrogen sensor. Observation of the curves obtained shows that the hydrogen sensor is most sensitive at the lowest pressures, in particular at 10 mbar. It is also seen that the sensitivity of the hydrogen sensor decreases with the value of the leakage rate, and is better for high leakage rates.

Figure 7:
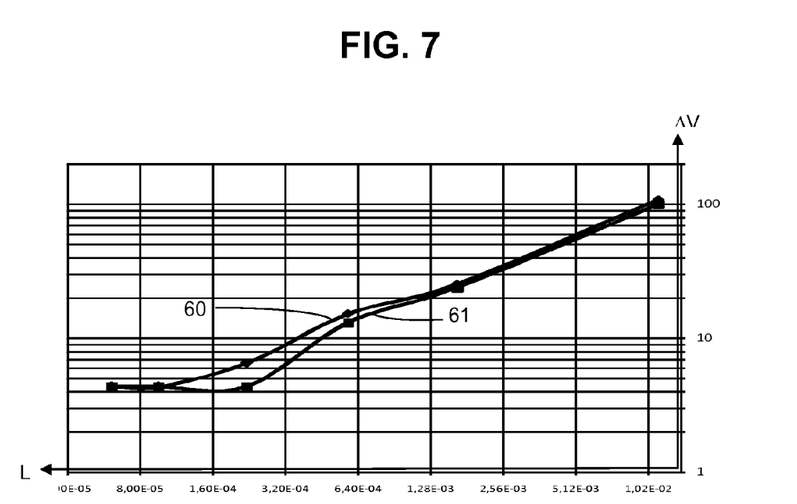
FIG. 7 illustrates the result of a sensitivity test of the hydrogen sensor for different distances between the leak and the hydrogen sensor and different leakage rates.

Thirdly, a test was carried out in order to identify the influence of the distance between the hydrogen sensor and the leak. FIG. 7 illustrates the result obtained. The curve 60 of voltage variation as a function of the leakage rate with a distance of 35 cm is very similar to the curve 61 obtained with a distance of 94 cm. The sensitivity of the hydrogen sensor is therefore influenced little by the position of the leak.

Figure 8:
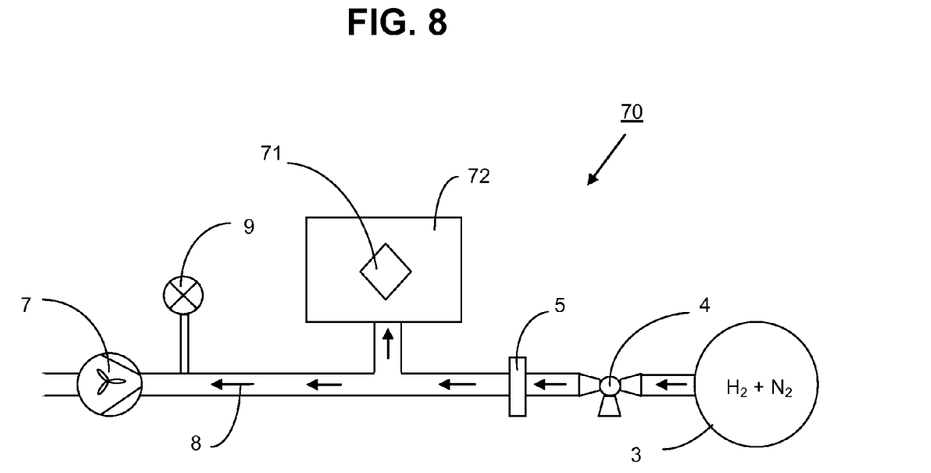
FIG. 8 illustrates another example of a test device intended to evaluate the sensitivity of a hydrogen sensor, as a function of its position with respect to the test gas flow.

Fourthly, the influence of the position of the hydrogen sensor in the detection device on its sensitivity was addressed. FIG. 8 illustrates the device 70 used for this test. This test device 70 is similar to the detection device of FIG. 1, except for the fact that the hydrogen sensor 71 and the low-pressure enclosure 72 which contains it are placed on a duct branching off from the main duct. The head of the hydrogen sensor 71 therefore no longer faces the main gas flow 8 containing hydrogen coming from the object 3 to be tested and pumped by the vacuum pump 7.

Figure 9:
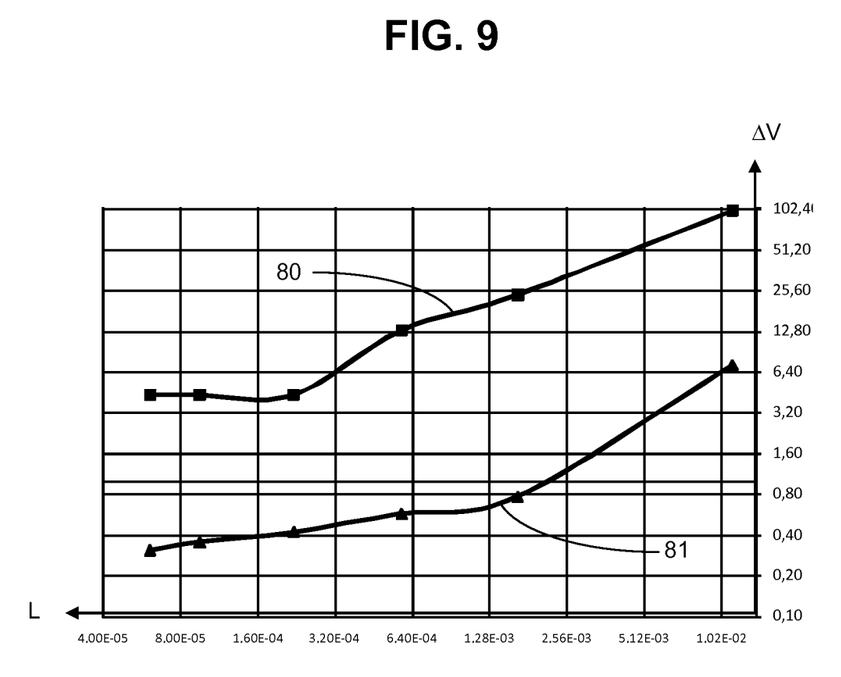
FIG. 9 illustrates the result of a sensitivity test of the hydrogen sensor for different positions in the leak detection device.

FIG. 9 shows the curves 80 and 81 corresponding respectively to the position of the hydrogen sensor 2 in FIG. 1 and the position of the sensor 71 in FIG. 8. This result confirms that the sensitivity of the hydrogen sensor 71 in FIG. 8 is less than that of the sensor 2 in FIG. 1. This result confirms that the hydrogen sensor should preferably be placed in a position such that its head faces the main gas flow 8 containing hydrogen coming from the object 3 to be tested and pumped by the pumping means 7.

The present invention is of course not limited to the embodiments described, but may be subject to numerous variants apparent to the person skilled in the art without departing from the spirit of the invention. In particular, the multiway valve may be a three-way valve, although it could also be replaced by two valves, for example each with two ports, or by any other means configured to place at least three ports, or even more than three ports, in communication. Furthermore, the low-pressure enclosure in which the sensor is placed may assume the form of a vacuum chamber, for example mechanically welded from stainless steel or aluminium, a pipeline portion closed in a leaktight fashion, or a cavity formed inside a block of material, for example by machining, or any other volume closed in a sufficiently leaktight manner to sustain a pressure substantially lower than the pressure prevailing in its immediate environment.

The invention claimed is:

1. A device for leak detection by means of hydrogen as a tracer gas, which device is intended to be connected to an object to be tested and comprises
    a hydrogen sensor placed in a low-pressure enclosure and comprising:
        a diode,
        a resistor and
        a MOS-type transistor whose gate is covered with a palladium catalyst,
    a pump connected to the low-pressure enclosure,
    a pressure gauge configured to measure the pressure in a vacuum line formed by the low-pressure enclosure connected to the pump,
    a multiway valve comprising a first port allowing admission of a gas flow containing the tracer gas into the vacuum line, and a second port allowing the admission of neutral gas,
    wherein the second port is configured to control the pressure in the vacuum line and said enclosure, as a function of the pressure gauge by controlling the admission of a neutral gas into the vacuum line through said second port;
    and wherein said leak detection device further comprises a circuit for balancing the voltage of the resistor of the hydrogen sensor, said circuit being configured to maintain a fixed temperature independently of the value of the pressure of the vacuum line, wherein said fixed temperature is between 100° C. and 250° C.

2. A leak detection device according to claim 1, wherein the second port is configured to be open to the external atmosphere.

3. A leak detection device according to claim 1, further comprising a particle filter interposed between the hydrogen sensor and the multiway valve in order to filter dust particles contained in the gas before it enters into contact with the hydrogen sensor.

4. A leak detection device according to claim 1, further comprising an electronic control module configured to receive the value of the pressure of the vacuum line measured by the pressure gauge, configured to receive a setpoint value and configured to control the admission of neutral gas as a function of these values.

5. A leak detection device according to claim 1, further comprising a mathematical model for calculating a leakage rate on the basis of the variation of the drain-source voltage of the transistor contained in the hydrogen sensor as a function of time.

6. A leak detection device according to claim 1, wherein the pressure in the low-pressure enclosure is between 100 Pa and 5000 Pa.

7. A leak detection device according to claim 1, wherein said pump is coupled to said enclosure downstream of said sensor and on a side of said enclosure opposite a side at which said tracer gas from said object to be tested.

8. A leak detection system according to claim 1, wherein said pump reduces the pressure in said enclosure.

9. A leak detection device according to claim 1, wherein said enclosure forms a portion of said vacuum line between said pump and said multi-way valve.

10. A device according to claim 1, wherein said second port admits neutral gas to maintain a desired pressure in said enclosure during operation of said sensor.

11. A method for leak detection of an object to be tested by means of a leak detection device, said leak detection device comprising: a hydrogen sensor placed in a low-pressure enclosure and comprising a diode, a resistor and a MOS-type transistor whose gate is covered with a palladium catalyst: a pump connected to the low-pressure enclosure; a pressure gauge configured to measure the pressure in a vacuum line formed by the low-pressure enclosure connected to the pump; and a multiway valve comprising a first port allowing admission of a gas flow containing a tracer gas into the vacuum line, and a second port allowing the admission of neutral gas, said method comprising the step of controlling the pressure of the vacuum line and said enclosure, as a function of the pressure gauge by controlling the admission of the neutral gas into the vacuum line through the second admission port of the multiway valve; and said method further comprising balancing the voltage of the resistor of the hydrogen sensor so as to maintain a fixed temperature independently of the value of the pressure of the vacuum line, wherein said fixed temperature is between 100° C. and 250° C.

12. A method for leak detection according to claim 11, wherein the admission of the neutral gas is controlled by controlling the second admission port automatically as a function of the measurement of the pressure and the value of a predetermined setpoint.

13. A leak detection method according to claim 11, wherein said pump is coupled to said enclosure downstream of said sensor and on a side of said enclosure opposite a side at which said tracer gas arrives from said object to be tested.

14. A leak detection method according to claim 11, wherein said pump reduces the pressure in said enclosure.

15. A leak detection method according to claim 11, wherein said enclosure forms a portion of said vacuum line between said pump and said multi-way valve.

16. A method according to claim 11, wherein said second port admits neutral gas to maintain a desired pressure in said enclosure during operation of said sensor.

\* \* \* \* \*